(12) United States Patent
Ichiyanagi et al.

(10) Patent No.: US 7,704,358 B2
(45) Date of Patent: Apr. 27, 2010

(54) OXYGEN SENSOR

(75) Inventors: Futoshi Ichiyanagi, Gunma (JP); Akira Uchikawa, Gunma (JP); Shoichi Sakai, Gunma (JP); Goji Matsumoto, Gunma (JP)

(73) Assignee: Hitachi, Ltd., Tokyo (JP)

( * ) Notice: Subject to any disclaimer, the term of this patent is extended or adjusted under 35 U.S.C. 154(b) by 468 days.

(21) Appl. No.: 11/711,775

(22) Filed: Feb. 28, 2007

(65) Prior Publication Data

US 2007/0199820 A1  Aug. 30, 2007

(30) Foreign Application Priority Data

Feb. 28, 2006  (JP) ............... 2006-052627

(51) Int. Cl.
*G01N 27/26* (2006.01)

(52) U.S. Cl. .............. 204/426; 204/427; 204/425; 29/745; 29/746

(58) Field of Classification Search ........ 204/424, 204/425, 426, 427, 428, 429; 29/729, 745, 29/746

See application file for complete search history.

(56) References Cited

U.S. PATENT DOCUMENTS 6,007,688 A * 12/1999 Kojima et al. ............ 204/426
6,889,536 B2 * 5/2005 Sakai et al. ............... 73/23.32
2003/0213696 A1 * 11/2003 Dardik ..................... 205/108

FOREIGN PATENT DOCUMENTS

JP  2004-239688 A  8/2004

* cited by examiner

*Primary Examiner*—Bruce F Bell
(74) *Attorney, Agent, or Firm*—Antonelli, Terry, Stout & Kraus, LLP.

(57) ABSTRACT

An oxygen sensor includes a base body portion; and a plurality of function layers laminated on a surface of the base body portion. The function layers includes a solid electrolyte layer adapted to conduct oxygen ions; a reference electrode layer located on a base body portion side of the solid electrolyte layer; a sensing electrode layer located on the opposite side of the solid electrolyte layer to the reference electrode layer; a heater portion adapted to activate the solid electrolyte layer by heating; and a gas diffusion layer formed between the reference electrode layer and the base body portion, and adapted to diffuse a reference gas within the gas diffusion layer. The gas diffusion layer is formed to have a porosity indicating a limit current value ranging between 60 µA and 200 µA. The limit current value is a value of a current flowing between the reference electrode layer and the sensing electrode layer when the current flowing therebetween becomes substantially constant during the process of bringing a voltage applied therebetween higher.

16 Claims, 4 Drawing Sheets

OXYGEN SENSOR

BACKGROUND OF THE INVENTION

The present invention relates to an oxygen sensor for sensing oxygen concentration, and its manufacturing method.

Japanese Patent published Application No. 2004-239688 discloses a previously proposed oxygen sensor. In the oxygen sensor disclosed in this Application, a heater pattern and an oxygen-ion-conducting solid electrolyte layer are formed on a base body portion in the oxygen sensor. The solid electrolyte layer formed by a pattern printing is activated by heating the heater pattern with applied current. Thus, oxygen concentration is sensed based on a potential difference between electrodes disposed opposite to each other through the solid electrolyte layer.

SUMMARY OF THE INVENTION

In the above technique, function layers including a heater layer and the solid electrolyte layer are formed by laminating disparate materials and then sintering this laminated materials. On the side of a reference electrode layer, a gas diffusion layer for introducing reference gas such as atmospheric air is also formed by pattern printing. However, a porosity of the gas diffusion layer formed by pattern printing is low which indicates a limit current value ranging about between 0.5 μA and 50 μA, when expressing the porosity by using the limit current value. Accordingly, the reference gas (atmospheric air) inside a sensor body cannot be sufficiently supplied or diffused to the reference electrode so that an oxygen partial pressure on the reference electrode side cannot be maintained. Hence in order to maintain the oxygen partial pressure on the reference electrode side, it has been required to supply or diffuse oxygen to the reference electrode by means of an injection current generated by an external circuit. The external circuit for applying the injection current is not compatible with a circuit for a so-called cup-type oxygen sensor which has been previously used before the pattern-printing-type oxygen sensor. Therefore, a new circuit for the pattern-printing-type oxygen sensor has been required.

It is therefore an object of the present invention to provide an oxygen sensor, devised to be capable of sensing with a simple circuit even if the function layers are formed by pattern printing, and devised not to reduce a yield of a sensor element.

According to one aspect of the present invention, there is provided an oxygen sensor comprising: a base body portion; and a plurality of function layers laminated on a surface of the base body portion, the function layers including a solid electrolyte layer adapted to conduct oxygen ions, a reference electrode layer located on a base body portion side of the solid electrolyte layer, a sensing electrode layer located on the opposite side of the solid electrolyte layer to the reference electrode layer, a heater portion adapted to activate the solid electrolyte layer by heating, and a gas diffusion layer formed between the reference electrode layer and the base body portion, and adapted to diffuse a reference gas within the gas diffusion layer, the gas diffusion layer being formed to have a porosity indicating a limit current value ranging between 60 μA and 200 μA, the limit current value being a value of a current flowing between the reference electrode layer and the sensing electrode layer when the current flowing therebetween becomes substantially constant during the process of bringing higher a voltage applied between the reference electrode layer and the sensing electrode layer.

According to another aspect of the present invention, there is provided an oxygen sensor comprising: a base body portion; and a plurality of function layers laminated on a surface of the base body portion, the function layers including a solid electrolyte layer adapted to conduct oxygen ions, a reference electrode layer located on a base body portion side of the solid electrolyte layer, a sensing electrode layer located on the opposite side of the solid electrolyte layer to the reference electrode layer, a heater portion adapted to activate the solid electrolyte layer by heating, and a gas diffusion layer formed between the reference electrode layer and the base body portion, and adapted to diffuse a reference gas within the gas diffusion layer, the gas diffusion layer being formed of a ceramic material and a vacancy forming material having an amount accounting for a ratio between 10% and 60% of a total amount of the ceramic material and the vacancy forming material in weight, the vacancy forming material being adapted to disappear when undergoing a sintering to form the gas diffusion layer as a porous ceramic layer.

According to still another aspect of the present invention, there is provided an oxygen sensor comprising: a base body portion; and a plurality of function layers laminated on a surface of the base body portion, the function layers including a solid electrolyte layer adapted to conduct oxygen ions, a reference electrode layer located on a base body portion side of the solid electrolyte layer, a sensing electrode layer located on the opposite side of the solid electrolyte layer to the reference electrode layer, a heater portion adapted to activate the solid electrolyte layer by heating, and a gas diffusion layer formed between the reference electrode layer and the base body portion, and adapted to diffuse a reference gas within the gas diffusion layer, the gas diffusion layer being formed of a ceramic material and a vacancy forming material having an amount accounting for a ratio between 20% and 80% of a total amount of the ceramic material and the vacancy forming material in volume, the vacancy forming material being adapted to disappear when undergoing a sintering to form the gas diffusion layer as a porous ceramic layer.

According to still another aspect of the present invention, there is provided a manufacturing method for an oxygen sensor including a base body portion; and a plurality of function layers laminated on a surface of the base body portion, the function layers including a solid electrolyte layer adapted to conduct oxygen ions, a reference electrode layer located on a base body portion side of the solid electrolyte layer, a sensing electrode layer located on the opposite side of the solid electrolyte layer to the reference electrode layer, a heater portion adapted to activate the solid electrolyte layer by heating, and a gas diffusion layer formed between the reference electrode layer and the base body portion, and adapted to diffuse a reference gas within the gas diffusion layer, the manufacturing method comprising: a first step of mixing a ceramic material with a vacancy forming material having an amount accounting for a ratio between 10% and 60% in weight or between 20% and 80% in volume relative to a total amount of ceramic material and vacancy forming material; and a second step of sintering the mixture to cause the vacancy forming material to disappear, thereby to form the gas diffusion layer as a porous ceramic layer.

The other objects and features of this invention will become understood from the following description with reference to the accompanying drawings.

DETAILED DESCRIPTION OF THE INVENTION

Figure 1:
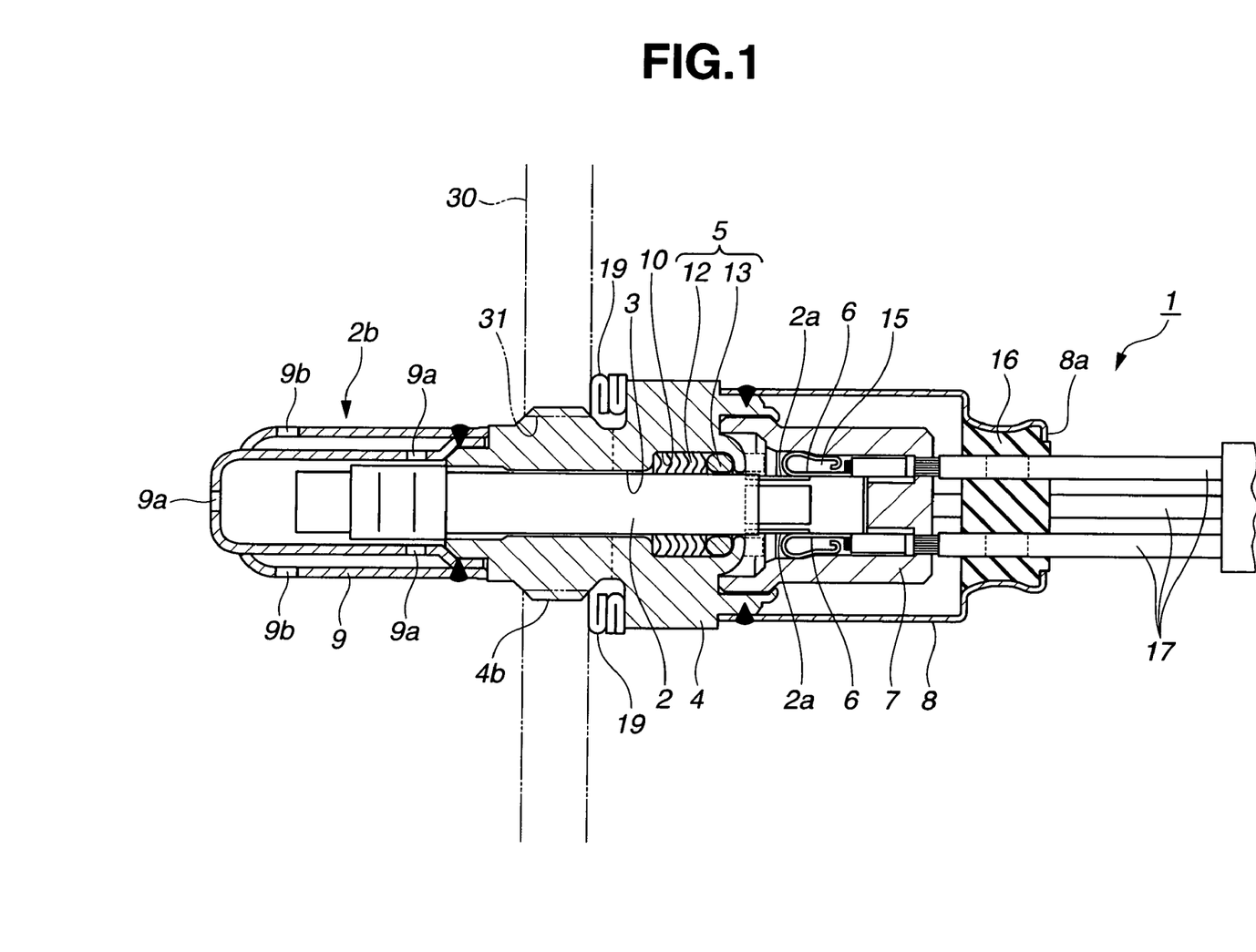
FIG. 1 is a sectional view of an oxygen sensor according to an embodiment of the present invention.

An embodiment of an oxygen sensor according to the present invention will now be explained in detail with reference to the accompanying drawings. The oxygen sensor in this embodiment is mounted to an exhaust pipe of an automobile equipped with an internal combustion engine, and used for detecting an air-fuel ratio. FIG. 1 is a sectional view of the oxygen sensor according to this embodiment.

A holder 4 is formed with a cylindrical-shaped element insertion hole (bore) 3. Into the cylindrical-shaped element insertion hole 3, a sensor element 2 shaped like a cylindrical rod is fit by insertion. The sensor element 2 extends through the element insertion hole 3, and outwardly projects from opposed axial end faces of the holder 4. Namely, the sensor element 2 passes through the holder 4 in the axial direction of element insertion hole 3. The sensor element 2 includes an oxygen measuring portion 2b formed at one axial end portion of sensor element 2, and an electrode(s) 2a at another axial end portion of sensor element 2. The oxygen measuring portion 2b of sensor element 2 is covered by or inserted inside a protector 9. The protector 9 has a tubular shape with a closed end, and is fixed with an axial end portion of holder 4 by a suitable method such as welding, caulking, or the like. The protector 9 has a double-tube (double-walled) structure which is constituted of an inner protector and an outer protector. The inner protector and outer protector of the protector 9 are formed with a plurality of inlet holes (circular holes) 9a and a plurality of inlet holes (circular holes) 9b for gas flow, respectively. A gas to be sensed is introduced into an inside space of the protector 9 through these inlet holes 9a and 9b, and reaches around the oxygen measuring portion 2b of sensor element 2.

The element insertion hole 3 has an increased-diameter portion 10 on the electrode 2a's side of element insertion hole 3. A sealing portion 5 disposed within this increased-diameter portion 10 keeps the airtightness at a clearance between the element insertion hole 3 and the sensor element 2. Namely, the sealing portion 5 fills the clearance between a circumferential surface of increased-diameter portion 10 and an outer circumferential surface of sensor element 2 to thereby hermetically seal the clearance. Concretely, the sealing portion 5 includes ceramic powder 12 (e.g., unsintered talc) and a spacer 13 (e.g., washer). To fill the clearance, the ceramic powder 12 is charged in the increased-diameter portion 10 of element insertion hole 3, and then is compacted or pushed to depth by using the spacer 13. A terminal support 7 for retaining terminals is fixed with the other axial end portion of holder 4 which is located on the side of electrode 2a of sensor element 2. The terminal support 7 is made of glass and formed into a cylindrical shape with a closed end. This terminal support 7 covers electrode 2a and the like of sensor element 2. Moreover, a tubular casing 8 is arranged so as to cover the terminal support 7 with a predetermined space between an inner circumferential surface of tubular casing 8 and an outer circumferential surface of terminal support 7. One axial end portion of tubular casing 8 is fixed to an outer circumferential surface of the other axial end portion of holder 4 by a suitable method such as laser welding (so-called laser welding-all-around). By such laser welding, casing 8 and holder 4 are connected together in a hermetically sealed relation to each other.

The other axial end portion of casing 8 which is located on the opposite side of oxygen measuring portion 2b is filled with a substantially-cylindrical seal rubber 16. The seal rubber 16 is fixed to the other axial end portion of casing 8 by a caulking portion 8a of casing 8. A plurality of leads 17 (e.g., four leads) are drawn to the outside of casing 8 so as to pass through the seal rubber 16. The seal rubber 16 ensures a hermetical seal between the leads 17 and the seal rubber 16, and a hermetical seal between the casing 8 and the seal rubber 16. Preferably, the seal rubber 16 is made of a high heat-resistant material such as fluororubber. Each of leads 17 has one end connected with a terminal(s) 6 which is retained inside terminal support 7 thereby. The terminal 6 is configured to be a resilient body (elastic body), and is more surely in contact with the electrode 2a formed on an outer peripheral surface of sensor element 2 by means of the resilient force. This can ensure continuity between the electrode 2a and the terminal 6.

Thus constructed oxygen sensor 1 is fixedly mounted to an exhaust pipe 30 by screwing a threaded portion 4b of the holder 4 into a tapped hole 31 which is formed in a circumferential wall of exhaust pipe 30. In the mounted state of oxygen sensor 1, a portion of oxygen sensor 1 which is covered with the protector 9 is projected into an exhaust passage inside the exhaust pipe 30. A gasket 19 is disposed between a flange of holder 4 and an outer surface of exhaust pipe 30, and seals a clearance between the oxygen sensor 1 and the exhaust pipe 30. An internal space 15 of oxygen sensor 1 which is formed inside the oxygen sensor 1, is prevented from being communicated with an outside of oxygen sensor 1 with cooperation of the sealing portion 5, the seal rubber 16, and the hermetic connection between holder 4 and casing 8. Namely, the internal space 15 ensures air tightness against the outside of oxygen sensor 1 at the areas of the sealing portion 5, the seal rubber 16, and the connection between holder 4 and casing 8. However, the internal space 15 is slightly in communication with the outside of oxygen sensor 1 through an extremely fine space inside the lead 17 (e.g., a clearance between a core and a coat of lead 17). Therefore, the internal space 15 is filled with an atmospheric air serving as a reference gas.

When an exhaust gas passing inside the exhaust pipe 30 flows into the inside space of oxygen sensor 1 through inlet holes 9a and inlet holes 9b of the protector 9, oxygen in the exhaust gas enters the oxygen measuring portion 2b of sensor element 2. Oxygen concentration of the exhaust gas is detected by the oxygen measuring portion 2b and converted into an electric signal indicative of this oxygen concentration. The electric signal is then outputted to the outside of oxygen sensor 1 via electrodes 2a, terminals 6, and leads 17.

The sensor element 2 includes a base body portion 100 shaped like a cylindrical rod, and function layers formed on a circumferential surface of base body portion 100. The function layers include a heater, a sensing portion, and the like. The base body portion 100 is made of a ceramic material such as alumina which is an insulating material, and is formed in a solid or hollow cylindrical shape. These function layers are constructed by burning each layer formed by way of screen printing in sequence. Now, each layer will be briefly explained referring to the sequence of printing on the rod surface (i.e., curved surface printing).

At first, an electrode-heater layer is printed including two pair of electrodes 2a and a heater pattern for activating the after-mentioned solid electrolyte layer by heating. On the heater pattern, a first protective layer which is made of an insulative material is printed for protecting this heater portion. One pair of electrodes 2a are connected with the heater pattern, and another pair of electrodes 2a are connected with the oxygen sensing portion shown in FIG. 2. After the printing of the heater portion, a printing of this oxygen sensing portion is carried out as follows. Namely, a gas diffusion layer (relaxation layer) 103 is printed to allow an end of gas diffusion layer 103 to reach one of the another pair of electrodes 2a. As mentioned below, the function layers including the gas diffusion layer 103 are finally sintered. Hence, the gas diffusion layer 103 contains a vacancy (cavity) forming material at the time of its printing, so as to cause the gas diffusion layer 103 to become a porous body after undergoing the sintering. In this embodiment, carbon particles are used as the vacancy forming material. However, the vacancy forming material is not limited to carbon particles, and the other material adapted to disappear at the time of sintering can be employed. Namely, the other material capable of being destroyed by fire can be employed.

In this embodiment, a ceramic material constituting the gas diffusion layer 103 is forced to contain the vacancy forming material, and then is printed. An average particle diameter of the vacancy forming material ranges from 1 µm to 20 µm. If the average particle diameter is smaller than 1 µm, the vacancy forming material cannot form a pore (gas-cavity) portion(s) having an effective size for the gas diffusion. If the average particle diameter is larger than 20 µm, the pore portion becomes too enlarged and thereby the gas diffusion layer 103 becomes fragile in itself.

A percentage content of the vacancy forming material against the ceramic material ranges from 10 wt % to 60 wt % of a sum amount of vacancy forming material and ceramic material in weight ratio, before undergoing the sintering. Namely, the vacancy forming material is mixed with the ceramic material, at the ratio (of vacancy forming material) ranging between 10 wt % and 60 wt % relative to the total weight of ceramic material and vacancy forming material. By so doing, a proper porosity can be achieved which indicates a limit current value ranging between 60 µA and 200 µA. If the percentage content is lower than 10 wt %, the porosity indicates a limit current value lower than 60 µA. If the percentage content is higher than 60 wt %, the porosity indicates a limit current value higher than 200 µA. In particular, a setting between 30 wt % and 50 wt % is more suitable within the range between 10 wt % and 60 wt %. In this range from 30 wt % to 50 wt %, both of the suitable limit current value and the suitable layer strength can be obtained in a proper balance.

On the other hand, in the case where the percentage content is represented in volume ratio instead of weight ratio, it is favorable that the vacancy forming material is mixed with the ceramic material at a ratio ranging between 20 Vol % and 80 Vol % of vacancy forming material relative to the total volume of ceramic material and vacancy forming material at the time before the sintering. By so doing, the proper porosity can be achieved which indicates the limit current value ranging between 60 µA and 200 µA. If the percentage content is lower than 20 Vol %, the porosity indicates a limit current value lower than 60 µA. If the percentage content is higher than 80 Vol %, the porosity indicates a limit current value higher than 200 µA. In particular, a setting between 50 Vol % and 70 Vol % is more suitable within the range between 20 Vol % and 80 Vol %. In this range from 50 Vol % to 70 Vol %, both of the suitable limit current value and the suitable layer strength can be obtained in a proper balance.

As mentioned above, the gas diffusion layer 103 becomes the porous body after undergoing the sintering. The gas diffusion layer 103 serves to diffuse the atmospheric air functioning as the reference gas from the above-mentioned internal space 15 (see FIG. 1) toward a lower area of a solid electrolyte layer 105. Next, an inner electrode layer (first or reference electrode layer) 104 is printed on the gas diffusion layer 103. One end (tip of a lead portion) of this inner electrode layer 104 reaches the electrode 2a. On another end (an inner electrode portion) of inner electrode layer 104, the solid electrolyte layer 105 is printed. In a printing process for the solid electrolyte layer 105, three layers are printed in piles sequentially. Namely, the solid electrolyte layer 105 includes the three (sub)layers.

The solid electrolyte layer 105 is formed, for example, by mixing a prescribed percentage (% by weight) amount of yttria powder with zirconia powder, then by processing the mixture into paste, and by carrying out a patterning of the mixture paste. At this time, the three layers of solid electrolyte layer 105 are formed, so as to cause one layer of solid electrolyte layer 105 which is near the base body portion 100 to be thicker than the other layer which is relatively apart from the base body portion 100. Namely, layer thicknesses of the three layers of solid electrolyte layer 105 are different from one another so that the layer thickness becomes larger toward the side of base body portion 100. Moreover, on an electrode 2a side of solid electrolyte layer 105, end portions of respective layers of solid electrolyte layer 105 are shifted or displaced from one another. Hence, the solid electrolyte layer 105 includes a stepwise portion formed by the end portions of three layers. The solid electrolyte layer 105 is printed so as to seal the gas diffusion layer 103 within a printing range of solid electrolyte layer 105.

Further, an outer electrode layer (second or sensing electrode layer) 106 is printed on a surface of top layer of solid electrolyte layer 105. At this time, one end (tip of a lead portion) of outer electrode layer 106 reaches the electrode 2a. Moreover, the lead portion of outer electrode layer 106 is printed on an upper surface of the above-mentioned stepwise portion of solid electrolyte layer 105. The inner electrode layer 104 and outer electrode layer 106 are respectively formed of a metallic material (e.g., platinum) having an electrical conductivity and also an oxygen permeability. The solid electrolyte layer 105 generates an electromotive force between the inner electrode layer 104 and the outer electrode layer 106, in accordance with a difference of oxygen concentrations in its surrounding area. Then, the solid electrolyte layer 105 transfers oxygen ions in a thickness direction of solid electrolyte layer 105. The inner electrode layer 104 is electrically connected with one of two leads among the four leads 17 (see FIG. 1), and the outer electrode layer 106 is electrically connected with another of the two leads. The output voltage generated between the inner electrode layer 104 and the outer electrode layer 106 can be detected as a voltage between these leads 17.

Next, a second protective layer (dense layer) 107 is printed on overall range of an upper surface of the function layers, except for the solid electrolyte layer 105 and the electrodes 2a (however, the second protective layer 107 reaches the stepwise portion of solid electrolyte layer 105). The second protective layer 107 protects the heater pattern and a wiring of the sensing portion (the lead portions of inner electrode layer 104 and outer electrode layer 106), and seals the gas diffusion layer 103. Since the second protective layer 107 seals the gas diffusion layer 103, an air leakage from the gas diffusion layer 103 can be reliably prevented. At last, a (second) diffusion layer is printed on overall range of an upper surface of the function layers including the solid electrolyte layer 105. This diffusion layer serves to protect the (oxygen) sensing portion, and serves to diffuse the exhaust gas inside the exhaust pipe of internal combustion engine up to the outer electrode layer 106. This diffusion layer becomes a porous body after undergoing the sintering.

According to this embodiment, the gas diffusion layer 103 is formed, by mixing the vacancy forming material such as carbon (disappearance agent) additionally with a mixed material of zirconia and aluminum, then by carrying out a patterning of this mixture, and then by burning this patterned mixture. Hence, the gas diffusion layer 103 has a porous structure as mentioned above. Therefore, oxygen (atmospheric air) introduced to the side of inner electrode layer 104 through the solid electrolyte layer 105 can enter the gas diffusion layer 103. The inner electrode layer 104 is formed, by mixing a vacancy forming material such as theobromine additionally with a precious metal material such as platinum, further by carrying out a patterning of this mixture, and further by burning this patterned mixture. Thus, since the inner electrode layer 104 is originally made to contain the vacancy forming material; the vacancy forming material (disappearance agent) disappears at the time of the burning, and cavities (vacancies) are formed within the inner electrode layer 104. Thereby, the electrode (layer) can have a porous structure.

The second protective layer 107 is formed of a material adapted not to transmit oxygen included in the gas to be sensed. For example, the second protective layer 107 is formed of a ceramic material such as alumina. The (second) diffusion layer is formed of a material adapted to transmit oxygen included in the gas to be sensed, and adapted not to transmit harmful gas, dust, and the like included in the gas to be sensed. For example, the diffusion layer is formed of a porous structural body such as a mixture of alumina and magnesium oxide. Note that a spinel protective layer (not shown) is formed further on the (second) diffusion layer. The spinel protective layer covers overall range of an outer surface of the sensor element, and is capable of transmitting oxygen included in the gas to be sensed, therethrough. The spinel protective layer is formed of a porous body coarser than the diffusion layer (i.e., more roughly-grained porous body than the second diffusion layer).

Figure 2:
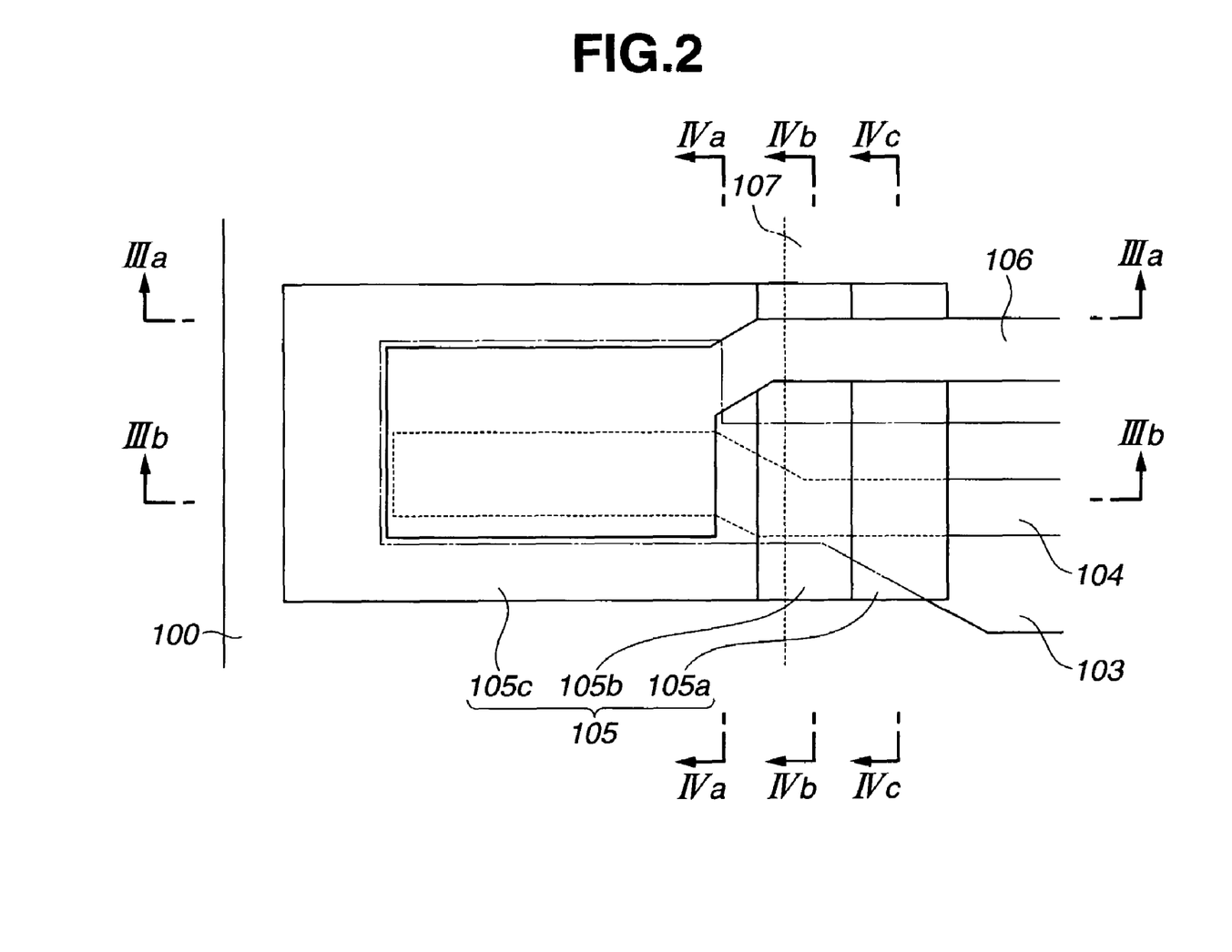
FIG. 2 is an enlarged developed view of a sensing portion in a sensor element of the oxygen sensor.
Figure 3A:
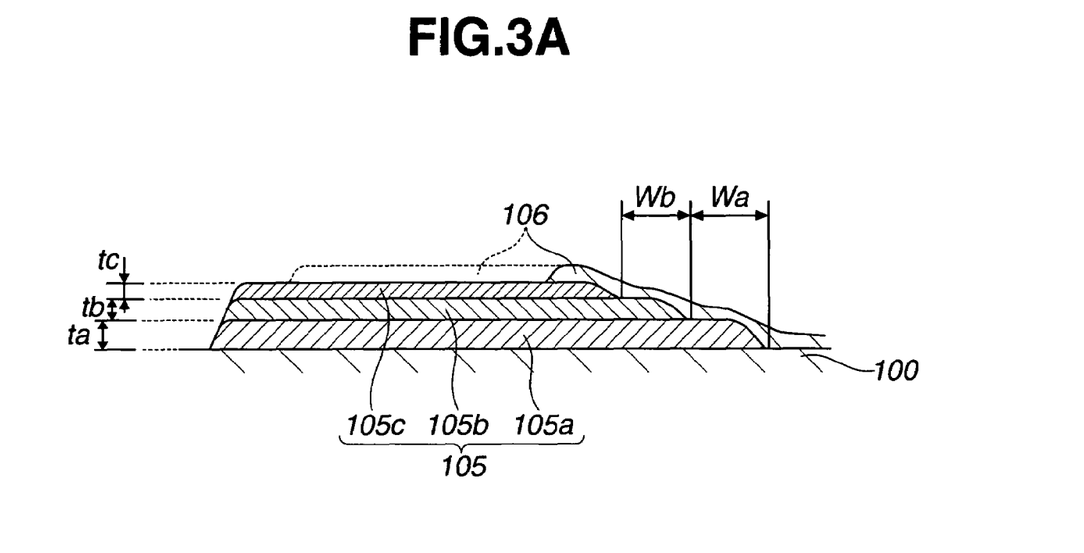
FIG. 3A is a sectional view of FIG. 2 taken along a line IIIa-IIIa.
Figure 3B:
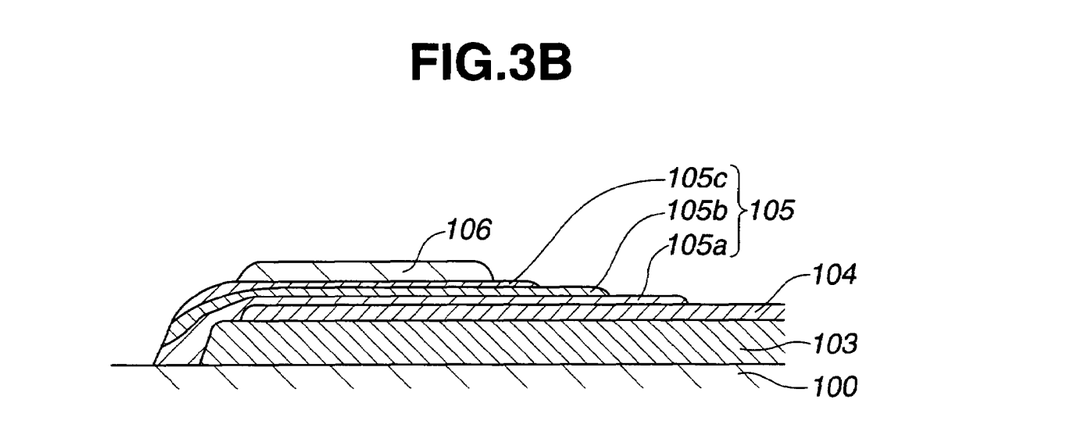
FIG. 3B is a sectional view of FIG. 2 taken along a line IIIb-IIIb.
Figure 4A:
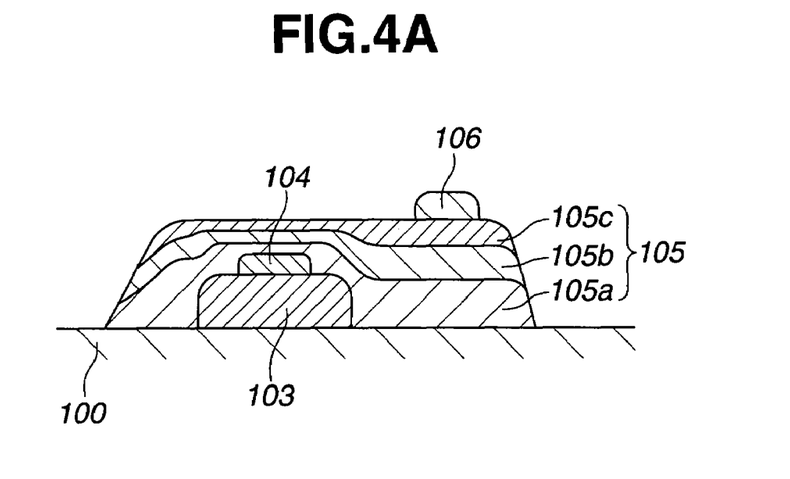
FIG. 4A is a sectional view of FIG. 2 taken along a line IVa-IVa.
Figure 4B:
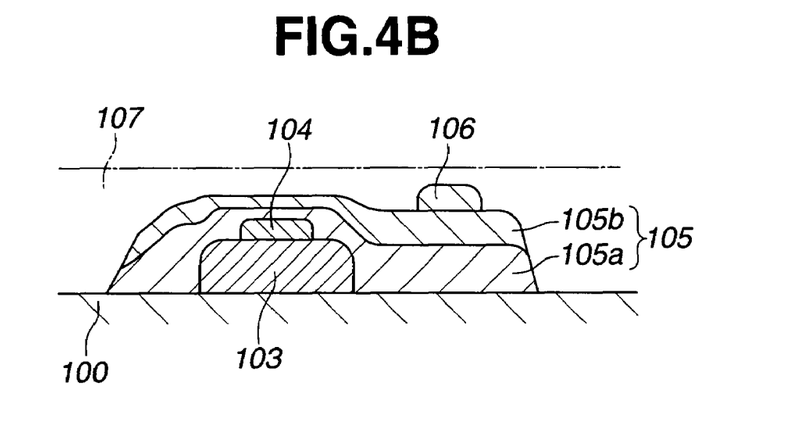
FIG. 4B is a sectional view of FIG. 2 taken along a line IVb-IVb.
Figure 4C:
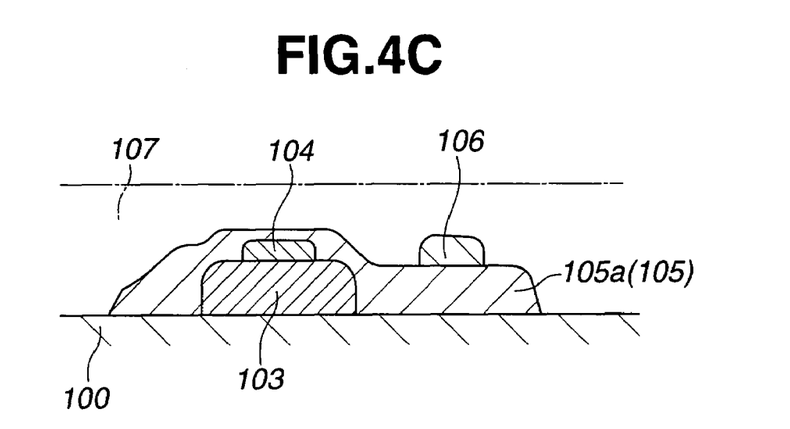
FIG. 4C is a sectional view of FIG. 2 taken along a line IVc-IVc.

FIG. 2 is an enlarged developed view of the sensing portion. In FIG. 2, the shapes of gas diffusion layer 103 and inner electrode layer 104 located (radially) inside of the solid electrolyte layer 105 are also shown respectively by an alternate-long-and-short-dash line and a dotted line. FIG. 3A is a sectional view of FIG. 2 taken along a line IIIa-IIIa, and FIG. 3B is a sectional view of FIG. 2 taken along a line IIIb-IIIb. Moreover, FIG. 4A is a sectional view of FIG. 2 taken along a line IVa-IVa, FIG. 4B is a sectional view of FIG. 2 taken along a line IVb-IVb, and FIG. 4C is a sectional view of FIG. 2 taken along a line IVc-IVc. Note that the surface of base body portion 100 is shown as a flat surface in FIGS. 4A to 4C for simplification, although it is actually a rounded surface.

As shown in FIGS. 2 to 4C, the solid electrolyte layer 105 (105a to 105c) is formed in a laminated manner, by way of three-times screen printings. Hence, a stress which occurs inside the solid electrolyte layer 105 when sintering the solid electrolyte layer 105 can be distributed to respective layers 105a to 105c. Therefore, a crack due to the inside stress can be prevented from occurring. Since the layer thickness ta~tc of each layer 105a~105c is designed to be thicker as the layer is located closer to the side of base body portion 100 (ta>tb>tc); the stress is relieved at the time of sintering, and the occurrence of crack can be prevented more efficiently. Furthermore as shown in FIG. 3A, the end portion of solid electrolyte layer 105 is formed in the stepwise manner when printing the solid electrolyte layer 105 in a plurality of stages (three stages). Then, the lead portion of outer electrode layer 106 is printed on the stepwise end portion of solid electrolyte layer 105, and thereby a drop of printing surface of the lead portion is moderated. Therefore, a wire disconnection or a print streaking of the lead portion (layer) is prevented.

Although the base body portion 100 is designed in the shape of circular cylinder in this embodiment; the base body portion 100 may be designed in the shape of a rod, having a rectangular cross section, and the function layers may be constructed on a surface of the square-rod-shaped base body portion 100 by the sintering after the screen printing. Furthermore in this embodiment, a length between steps of the stepwise portion (Wa or Wb shown in FIG. 3A) is designed to be longer than or equal to 300 μm. Namely, respective layers of solid electrolyte layer 105 are printed during the process of printing the solid electrolyte layer, so as to cause each length between three steps (length between axial ends of adjacent two layers) to become longer than or equal to 300 μm. Thereby, a contact area between the lead portion of outer electrode layer 106 and the respective layers 105a to 105c of solid electrolyte layer 105 becomes sufficiently large, and the disconnection or delamination of the lead portion can be reliably prevented.

Now, representative structures and effects according to this embodiment will be described in summary.

According to this embodiment, the oxygen sensor 1 includes the base body portion 100; and a plurality of function layers laminated on the surface of base body portion 100. This function layers include the solid electrolyte layer 105 adapted to conduct oxygen ions, the reference electrode layer 104 located on the base body portion side of solid electrolyte layer 105, the sensing electrode layer 106 located on the opposite side of solid electrolyte layer 105 to the reference electrode layer 104, the heater portion adapted to activate the solid electrolyte layer 105 by heating, and the gas diffusion layer 103 formed between the reference electrode layer 104 and the base body portion 100, and adapted to diffuse the reference gas within the gas diffusion layer 103. This gas diffusion layer 103 is formed to have a porosity indicating a limit current value ranging between 60 μA and 200 μA. This limit current value is a value of a current flowing between the reference electrode layer 104 and the sensing electrode layer 106 when the current flowing therebetween becomes substantially constant during the process of bringing a voltage applied therebetween higher.

Here, when a load voltage applied between the sensing electrode and the reference electrode is brought or swept higher, a value of the current flowing between the both electrodes becomes a constant value. This phenomenon occurs because the amount of oxygen which is being supplied to the reference electrode by the gas diffusion layer reaches its upper limit. This (constant) upper limit current value is called "limit current value". Since the upper limit of oxygen supply amount in the gas diffusion layer correlates with the porosity of gas diffusion layer, the porosity of gas diffusion layer can be expressed by the limit current value.

According to this embodiment, the oxygen sensor 1 includes the gas diffusion layer 103 formed of the ceramic material and the vacancy forming material having an amount accounting for a ratio between 10% and 60% of the total amount of ceramic material and vacancy forming material in weight. This vacancy forming material is adapted to disappear when undergoing the sintering to form the gas diffusion layer 103 as a porous ceramic layer.

According to this embodiment, the oxygen sensor 1 includes the gas diffusion layer 103 formed of the ceramic material and the vacancy forming material having an amount accounting for a ratio between 20% and 80% of the total amount of ceramic material and vacancy forming material in volume. This vacancy forming material is adapted to disappear when undergoing the sintering to form the gas diffusion layer 103 as a porous ceramic layer.

Next, the representative effects are as follows. In the oxygen sensor according to this embodiment, the gas diffusion layer is formed to make its porosity between 60 µA and 200 µA when expressing the porosity by using the limit current value. Accordingly, a sufficient oxygen can be supplied to the reference electrode, and the oxygen sensor can properly sense oxygen without the necessity to provide an external circuit for supplying an injection current (which serves to transmit additional oxygen to the reference electrode) or the like. If the porosity of the gas diffusion layer is designed to indicate a value lower than 60 µA as the limit current value; the diffusion of reference gas within the gas diffusion layer (i.e., on the reference electrode side) becomes insufficient, so that the output power is reduced. In order to compensate for this, the external circuit for supplying the injection current or the like is necessary. On the other hand, if the porosity of the gas diffusion layer is designed to indicate a value larger than 200 µA as the limit current value; the layer thickness becomes too thick, and the crack due to the inside stress becomes easy to occur at the time of the sintering. Moreover, e.g., in the case where the pore (vacancy) is formed by adding the vacancy forming material such as carbon particles; the amount of vacancy forming material is increased, and the yield of sensor element is worsened.

This application is based on a prior Japanese Patent Application No. 2006-052627 filed on Feb. 28, 2006. The entire contents of this Japanese Patent Application are hereby incorporated by reference.

Although the invention has been described above with reference to certain embodiments of the invention, the invention is not limited to the embodiments described above. Modifications and variations of the embodiments described above will occur to those skilled in the art in light of the above teachings. The scope of the invention is defined with reference to the following claims.

What is claimed is:

1. An oxygen sensor comprising:
a base body portion; and
a plurality of function layers laminated on a surface of the base body portion, the function layers including
a solid electrolyte layer adapted to conduct oxygen ions,
a reference electrode layer located on a base body portion side of the solid electrolyte layer,
a sensing electrode layer located on the opposite side of the solid electrolyte layer to the reference electrode layer,
a heater portion adapted to activate the solid electrolyte layer by heating, and
a gas diffusion layer formed between the reference electrode layer and the base body portion, and adapted to diffuse a reference gas within the gas diffusion layer,
the gas diffusion layer being formed to have a porosity indicating a limit current value ranging between 60 µA and 200 µA, the limit current value being a value of a current flowing between the reference electrode layer and the sensing electrode layer when the current flowing therebetween becomes substantially constant during the process of bringing higher a voltage applied between the reference electrode layer and the sensing electrode layer.

2. The oxygen sensor as claimed in claim 1, wherein
the gas diffusion layer is formed of a ceramic material and a vacancy forming material having an amount accounting for a ratio between 10% and 60% of a total amount of the ceramic material and the vacancy forming material in weight;
an average particle diameter of the vacancy forming material ranges from 1 µm to 20 µm; and
the vacancy forming material is adapted to disappear when undergoing a sintering to form the gas diffusion layer as a porous ceramic layer.

3. The oxygen sensor as claimed in claim 2, wherein the ratio is defined by a content of the vacancy forming material relative to the ceramic material before undergoing the sintering.

4. The oxygen sensor as claimed in claim 2, wherein the gas diffusion layer is formed of the ceramic material and the vacancy forming material having an amount accounting for a ratio between 30% and 50% of the total amount of the ceramic material and the vacancy forming material in weight.

5. The oxygen sensor as claimed in claim 1, wherein
the gas diffusion layer is formed of a ceramic material and a vacancy forming material having an amount accounting for a ratio between 20% and 80% of a total amount of the ceramic material and the vacancy forming material in volume;
an average particle diameter of the vacancy forming material ranges from 1 µm to 20 µm; and
the vacancy forming material is adapted to disappear when undergoing a sintering to form the gas diffusion layer as a porous ceramic layer.

6. The oxygen sensor as claimed in claim 1, wherein the solid electrolyte layer includes a plurality of laminated sublayers.

7. The oxygen sensor as claimed in claim 5, wherein the gas diffusion layer is formed of the ceramic material and the vacancy forming material having an amount accounting for a ratio between 50% and 70% of the total amount of the ceramic material and the vacancy forming material in volume.

8. An oxygen sensor comprising:
a base body portion; and
a plurality of function layers laminated on a surface of the base body portion, the function layers including
a solid electrolyte layer adapted to conduct oxygen ions,
a reference electrode layer located on a base body portion side of the solid electrolyte layer,
a sensing electrode layer located on the opposite side of the solid electrolyte layer to the reference electrode layer,
a heater portion adapted to activate the solid electrolyte layer by heating, and
a gas diffusion layer formed between the reference electrode layer and the base body portion, and adapted to diffuse a reference gas within the gas diffusion layer,
the gas diffusion layer being formed of a ceramic material and a vacancy forming material having an amount accounting for a ratio between 10% and 60% of a total amount of the ceramic material and the vacancy forming material in weight, the vacancy forming material being adapted to disappear when undergoing a sintering to form the gas diffusion layer as a porous ceramic layer.

9. The oxygen sensor as claimed in claim 8, wherein
the gas diffusion layer is formed of the ceramic material and the vacancy forming material having an amount accounting for a ratio between 30% and 50% of the total amount of the ceramic material and the vacancy forming material in weight under a state before the sintering.

10. The oxygen sensor as claimed in claim 8, wherein an average particle diameter of the vacancy forming material ranges from 1 μm to 20 μm.

11. An oxygen sensor comprising:
a base body portion; and
a plurality of function layers laminated on a surface of the base body portion, the function layers including
a solid electrolyte layer adapted to conduct oxygen ions,
a reference electrode layer located on a base body portion side of the solid electrolyte layer,
a sensing electrode layer located on the opposite side of the solid electrolyte layer to the reference electrode layer,
a heater portion adapted to activate the solid electrolyte layer by heating, and
a gas diffusion layer formed between the reference electrode layer and the base body portion, and adapted to diffuse a reference gas within the gas diffusion layer,
the gas diffusion layer being formed of a ceramic material and a vacancy forming material having an amount accounting for a ratio between 20% and 80% of a total amount of the ceramic material and the vacancy forming material in volume, the vacancy forming material being adapted to disappear when undergoing a sintering to form the gas diffusion layer as a porous ceramic layer.

12. The oxygen sensor as claimed in claim 11, wherein
the gas diffusion layer is formed of the ceramic material and the vacancy forming material having an amount accounting for a ratio between 50% and 70% of the total amount of the ceramic material and the vacancy forming material in volume under a state before the sintering.

13. The oxygen sensor as claimed in claim 11, wherein an average particle diameter of the vacancy forming material ranges from 1 μm to 20 μm.

14. A manufacturing method for an oxygen sensor including
a base body portion; and
a plurality of function layers laminated on a surface of the base body portion, the function layers including
a solid electrolyte layer adapted to conduct oxygen ions,
a reference electrode layer located on a base body Portion side of the solid electrolyte layer,
a sensing electrode layer located on the opposite side of the solid electrolyte layer to the reference electrode layer,
a heater portion adapted to activate the solid electrolyte layer by heating, and
a gas diffusion layer formed between the reference electrode layer and the base body portion, and adapted to diffuse a reference gas within the gas diffusion layer,
the manufacturing method comprising:
a first step of mixing a ceramic material with a vacancy forming material having an amount accounting for a ratio between 10% and 60% in weight or between 20% and 80% in volume relative to a total amount of ceramic material and vacancy forming material; and
a second step of sintering the mixture to cause the vacancy forming material to disappear, thereby to form the gas diffusion layer as a porous ceramic layer.

15. The manufacturing method as claimed in claim 14, wherein in the first step,
a ceramic material is mixed with the vacancy forming material having an amount accounting for a ratio between 30% and 50% in weight or between 50% and 70% in volume relative to the total amount of ceramic material and vacancy forming material.

16. The manufacturing method as claimed in claim 14, wherein in the first step,
an average particle diameter of the vacancy forming material ranges from 1 μm to 20 μm.

* * * * *